(12) United States Patent
King

(10) Patent No.: US 7,146,223 B1
(45) Date of Patent: Dec. 5, 2006

(54) METHOD FOR OPTIMIZING SEARCH FOR SPINAL CORD STIMULATION PARAMETER SETTINGS

(75) Inventor: John D. H. King, Sherman Oaks, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 530 days.

(21) Appl. No.: 10/355,955

(22) Filed: Jan. 31, 2003

Related U.S. Application Data

(60) Provisional application No. 60/354,098, filed on Feb. 4, 2002.

(51) Int. Cl.
*A61N 1/04* (2006.01)

(52) U.S. Cl. .................. 607/117; 607/118; 607/30; 607/60; 128/920

(58) Field of Classification Search .............. 607/27, 607/30, 59, 60, 117, 118; 128/920
See application file for complete search history.

(56) References Cited

U.S. PATENT DOCUMENTS

| | | | |
|---|---|---|---|
| 3,646,940 A | 3/1972 | Timm et al. |
| 3,724,467 A | 4/1973 | Avery et al. |
| 3,822,708 A | 7/1974 | Zilber |
| 4,019,518 A | 4/1977 | Maurer et al. |
| 4,520,825 A | 6/1985 | Thompson et al. |
| 4,793,353 A | 12/1988 | Borkan |
| 5,167,229 A | 12/1992 | Peckham et al. |
| 5,354,320 A | 10/1994 | Schaldach et al. |
| 5,370,672 A | 12/1994 | Fowler et al. |
| 5,417,719 A | 5/1995 | Hull et al. |
| 5,443,486 A | 8/1995 | Hrdlicka et al. |
| 5,501,703 A | 3/1996 | Holsheimer et al. |
| 5,601,617 A | 2/1997 | Loeb et al. |
| 5,626,629 A | 5/1997 | Faltys et al. |
| 5,643,330 A | 7/1997 | Holsheimer et al. |
| 5,649,970 A | 7/1997 | Loeb et al. |
| 5,674,264 A | 10/1997 | Carter et al. |
| 5,713,922 A | 2/1998 | King |
| 5,776,171 A | 7/1998 | Peckham et al. |
| 5,776,172 A | 7/1998 | Schulman et al. |
| 5,814,092 A | 9/1998 | King |
| 5,913,882 A | 6/1999 | King |
| 5,938,690 A | 8/1999 | Law et al. |

(Continued)

FOREIGN PATENT DOCUMENTS

EP  0811395 A2  10/1997

(Continued)

*Primary Examiner*—Robert E. Pezzuto
*Assistant Examiner*—Tammie K. Heller
(74) *Attorney, Agent, or Firm*—Vista IP Law Group LLP

(57) ABSTRACT

A method for selecting Spinal Cord Stimulation (SCS) stimulation parameter sets guides a clinician towards an effective set of stimulation parameters. The clinician first evaluates the effectiveness of a small number of trial stimulation parameter sets from a Measurement Table. Based on the patient's assessment, the trial stimulation sets are ranked. Then the clinician selects a starting or benchmark row in a Steering Table corresponding to the highest ranked trial stimulation parameter set. The clinician moves either up or down from the starting row, testing consecutive parameter sets. When a local optimum is found, the clinician returns to the benchmark row, and tests in the opposite direction for another local optimum. This process of searching for optimum parameter sets is repeated for a new starting row in the Steering Table that is selected based on the next ranked trial set from the Measurement Table.

30 Claims, 2 Drawing Sheets

U.S. PATENT DOCUMENTS

| | | |
|---|---|---|
| 6,052,624 A | 4/2000 | Mann |
| 6,393,325 B1 | 5/2002 | Mann et al. |
| 6,516,227 B1 | 2/2003 | Meadows et al. |
| 6,546,290 B1 | 4/2003 | Shloznikov |
| 6,600,954 B1 | 7/2003 | Cohen et al. |
| 6,609,031 B1 | 8/2003 | Law et al. |
| 6,609,032 B1 | 8/2003 | Woods et al. |
| 6,622,048 B1 * | 9/2003 | Mann et al. ............... 607/46 |
| 6,792,310 B1 * | 9/2004 | Turcott et al. ............... 607/27 |
| 2004/0082980 A1 | 4/2004 | Mouine et al. |
| 2004/0143303 A1 | 7/2004 | Sieracki et al. |
| 2004/0215288 A1 | 10/2004 | Lee et al. |

FOREIGN PATENT DOCUMENTS

| | | |
|---|---|---|
| WO | WO 01/43818 A1 | 6/2001 |
| WO | WO 04/041351 A1 | 5/2004 |

* cited by examiner

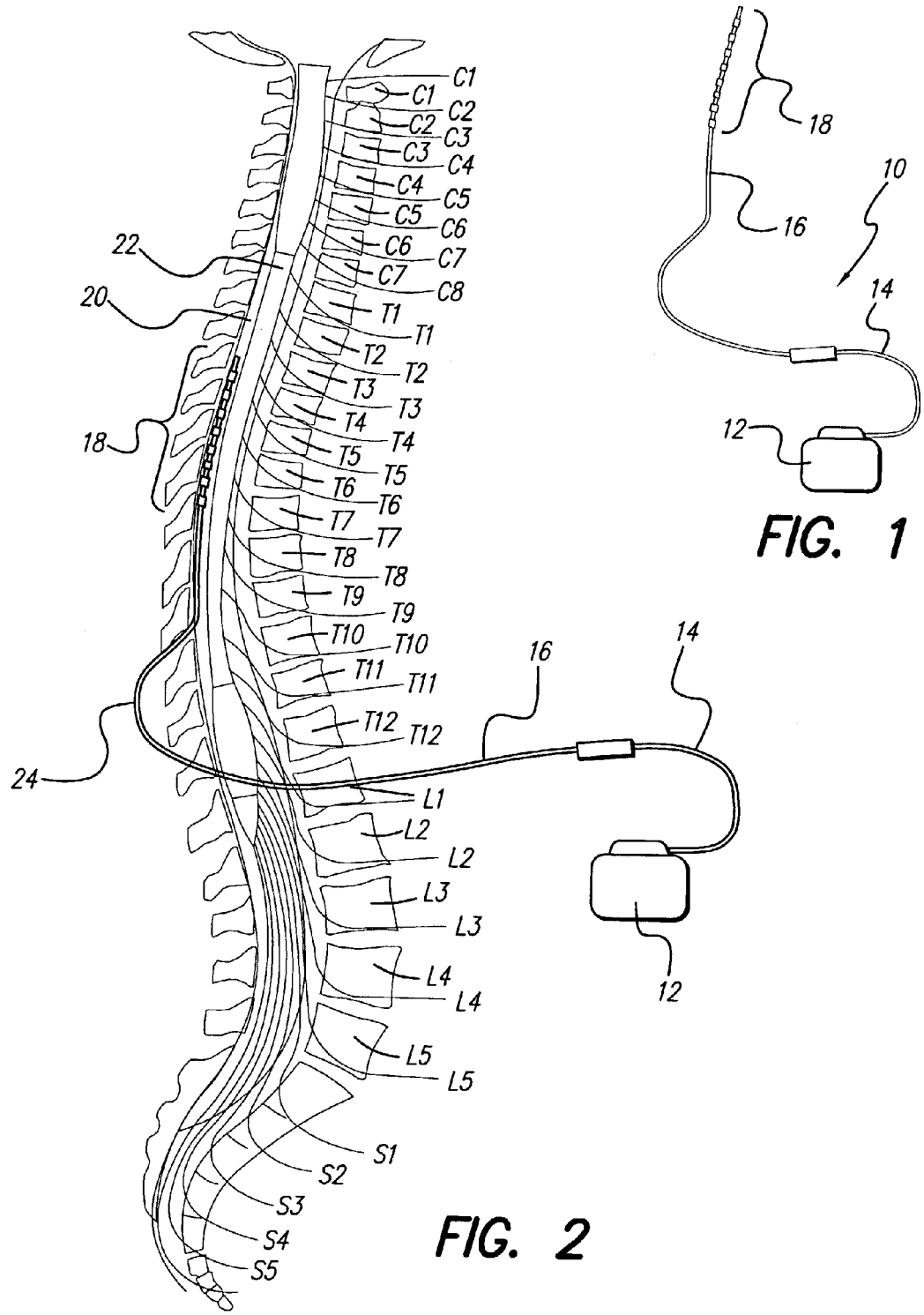

METHOD FOR OPTIMIZING SEARCH FOR SPINAL CORD STIMULATION PARAMETER SETTINGS

This application claims the benefit of U.S. Provisional Application Ser. No. 60/354,098, filed 4 Feb. 2002, which application is incorporated herein by reference.

BACKGROUND OF THE INVENTION

The present invention relates to Spinal Cord Stimulation (SCS) systems and more particularly to a method for efficiently searching for an effective SCS system stimulation parameter set. An SCS system treats chronic pain by providing electrical stimulation pulses through the electrodes of an electrode array placed epidurally next to a patient's spinal cord. The stimulation parameter set determines the characteristics of the stimulation pulses provided through the electrode array, and the electrodes used to provide the stimulation pulses. The optimal stimulation parameter set for a specific patient may be determined from the response of the patient to various sets of stimulation parameters. There is however, an extremely large number of possible combinations of stimulation parameters, and evaluating all possible sets is very time consuming, and impractical.

Spinal cord stimulation is a well accepted clinical method for reducing pain in certain populations of patients. An SCS system typically includes an Implantable Pulse Generator (IPG), electrodes, electrode lead, and electrode lead extension. The electrodes are implanted along the dura of the spinal cord, and the IPG generates electrical pulses that are delivered, through the electrodes, to the dorsal column fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and generally attach to one or more electrode lead extensions. The electrode lead extensions, in turn, are typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of The Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes which are positioned longitudinally on the spinal cord. Electrical pulses applied to the electrodes block perceived intractable pain, while allowing passage of other sensations. A patient operated switch allows the patient to adjust the stimulation parameters.

Most of the electrode arrays used with known SCS systems employ between 4 and 16 electrodes. Electrodes are selectively programmed to act as anodes, cathodes, or left off, creating a stimulating group. The number of stimulation groups available, combined with the ability of integrated circuits to generate a variety of complex stimulation pulses, presents a huge selection of stimulation parameter sets to the clinician. When an SCS system is implanted, a fitting procedure is performed to select an effective stimulation parameter set for a particular patient.

A known practice is to manually test one parameter set, and then select a new stimulation parameter set to test, and compare the results. Each parameter set is painstakingly configured, and ramped up in amplitude gradually to avoid patient discomfort. The clinician bases their selection of a new stimulation parameter set on their personal experience and intuition. There is no systematic method to guide the clinician. If the selected stimulation parameters are not an improvement, the clinician repeats these steps, using a new stimulation parameter set, based only on dead-reckoning. The combination of the time required to test each parameter set, and the number of parameter sets tested, results in a very time consuming process.

What is needed is a method for selection of trial stimulation parameter sets that guides the clinician towards an effective stimulation parameter set.

SUMMARY OF THE INVENTION

The present invention addresses the above and other needs by providing a method for selecting trial Spinal Cord Stimulation (SCS) stimulation parameter sets, which method guides a clinician towards an effective set of stimulation parameters.

In accordance with one aspect of the invention, there is provided a table, or equivalent, of a small number of trial stimulation parameter sets (a course table) that defines a starting point for selecting a stimulation parameter set. There is also provided a larger table (a fine table), or equivalent, of predetermined stimulation parameter sets to guide the search for a local optimum. Any method for finding an effective stimulation parameter set that uses a combination of a small course table, or equivalent, and a large fine table, or equivalent, is intended to come within the scope of the invention.

In accordance with another aspect of the invention, the clinician first evaluates the effectiveness of a small number of trial stimulation parameter sets from a Simplified Measurement Table comprising for example, four stimulation parameter sets. Based on the patient's assessment, the trial stimulation sets are ranked. Then the clinician selects a starting row in a Simplified Steering Table corresponding to the highest ranked trial stimulation parameter set. The clinician moves either up or down from the starting row, testing consecutive parameter sets. The clinician continues as long as the patient indicates that the stimulation results are improving. When a local optimum is found, the clinician returns to the starting row, and tests in the opposite direction for another local optimum. If an acceptable set of stimulation parameters is found, the selection process is complete. If an acceptable set is not found, a new starting row in the Simplified Steering Table is selected based on the next best trial stimulation parameter set, and the process of searching for local optima is repeated.

In accordance with yet another aspect of the invention, there is provided a method for searching for an effective set of stimulation parameters for an SCS system. The method improves the efficiency of the search by organizing the search based on predetermined stimulation parameter sets. A clinician first ranks the effectiveness of a very small set of trial stimulation parameter sets, and then searches for an optimum stimulation set around the highest ranked trial stimulation parameter set.

It is thus a feature of the present invention to provide a method for determining a locally optimum SCS system stimulation parameter set without requiring exhaustive testing of a multiplicity of stimulation parameter sets. Millions of possible stimulation parameter sets exist, and it is therefore impossible to test all possible sets. Therefore the clinician must be satisfied by finding an effective stimulation parameter set. By providing a systematic method for searching for an effective stimulation parameter set, a locally optimum stimulation parameter set is found, which locally optimum stimulation parameter set is associated with a best trial stimulation parameter set.

BRIEF DESCRIPTION OF THE DRAWINGS

The above and other aspects, features and advantages of the present invention will be more apparent from the following more particular description thereof, presented in conjunction with the following drawings wherein:

FIG. 1 shows a Spinal Cord Stimulation (SCS) system;

FIG. 2 depicts the SCS system of FIG. 1 implanted in a spinal column; and

Corresponding reference characters indicate corresponding components throughout the several views of the drawings.

Figure 3:
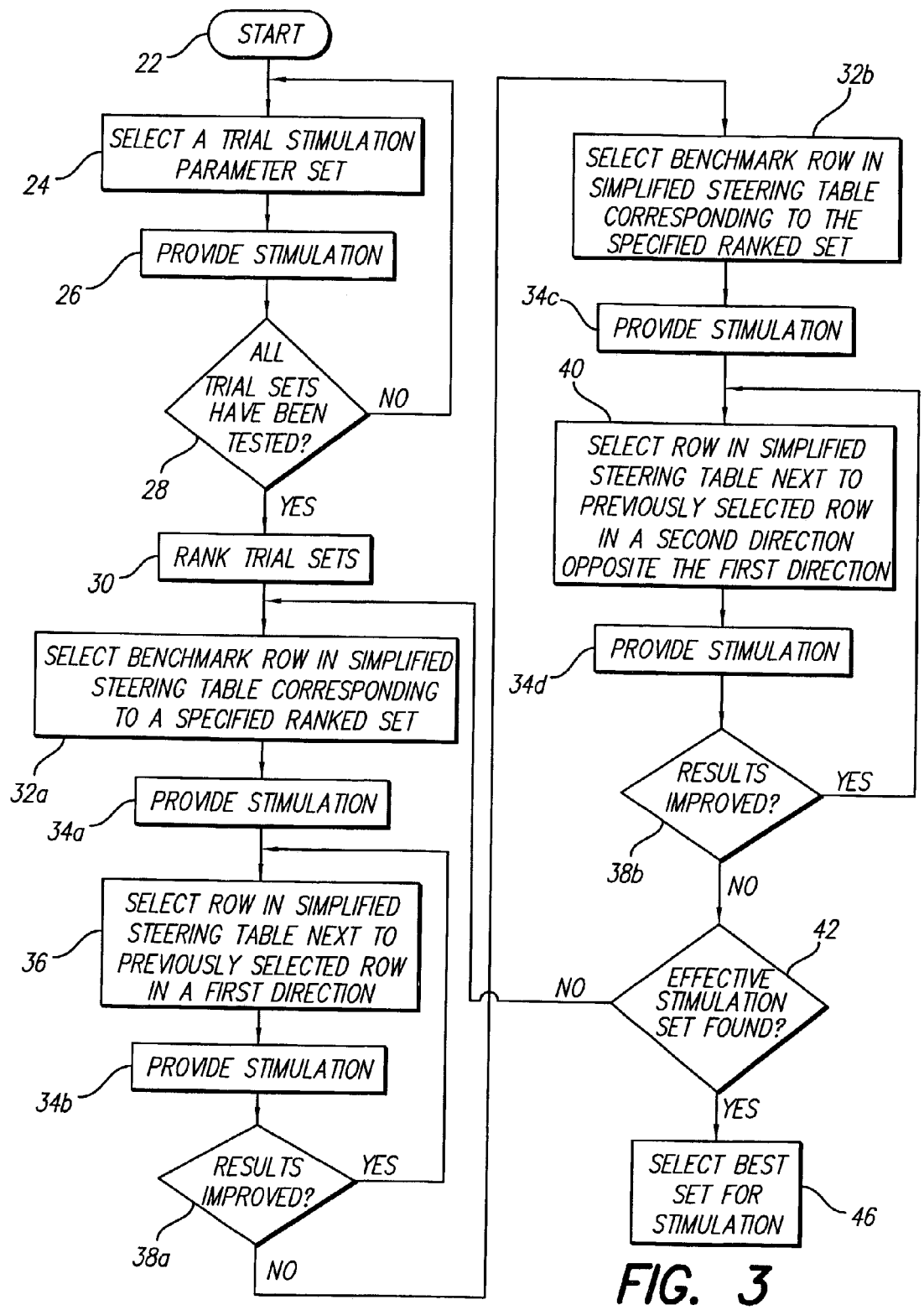
FIG. 3 depicts a stimulation parameter set flow chart according to one embodiment of the present invention.

Appendix A, comprising 2 pages including a cover, is an example of a Simplified Measurement Table.

Appendix B, comprising 13 pages including a cover, is an example of a Simplified Steering Table.

Appendices A and B are incorporated herein by reference.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The method of the present invention provides a systematic approach for selecting a Spinal Cord Stimulation (SCS) parameter set. The method leads a clinician through a selection process that efficiently locates locally optimum stimulation parameter sets.

A typical Spinal Cord Stimulation (SCS) system 10 is shown in FIG. 1. The SCS system 10 typically comprises an Implantable Pulse Generator (IPG) 12, a lead extension 14, an electrode lead 16, and an electrode array 18. The IPG 12 generates stimulation current for implanted electrodes that make up the electrode array 18. A proximal end of the lead extension 14 is removably connected to the IPG 12 and a distal end of the lead extension 14 is removably connected to a proximal end of the electrode lead 16, and electrode array 18 is formed on a distal end of the electrode lead 16. The in-series combination of the lead extension 14 and electrode lead 16, carry the stimulation current from the IPG 12 to the electrode array 18.

The SCS system 10 described in FIG. 1 above, is depicted implanted in the epidural space 20 in FIG. 2. The electrode array 18 is implanted at the site of nerves that are the target of stimulation, e.g., along the spinal cord. Due to the lack of space near the location where the electrode lead 16 exits the spinal column, the IPG 12 is generally implanted in the abdomen or above the buttocks. The lead extension 14 facilitates locating the IPG 12 away from the electrode lead exit point.

A more detailed description of a representative SCS system that may be used with the present invention is described in U.S. Pat. No. 6,516,227, to issue 4 Feb. 2003, incorporated herein by reference. It is to be emphasized, however, that the invention herein described may be used with many different types of stimulation systems, and is not limited to use only with the representative SCS system described in the U.S. Pat. No. 6,516,227 patent.

A flow chart representing one embodiment of a method for stimulation parameter set selection in accordance with the present invention is depicted in FIG. 3. As with most flow charts, each step or act of the method is represented in a "box" or "block" of the flow chart. Each box or block, in turn, has a reference number associated with it to help explain the process in the description that follows.

At the start 22 of the method, a measurement table, or equivalent, and a steering table, or equivalent, are provided. The measurement table typically comprises rows, with each row defining one set of stimulation parameters. In a preferred embodiment, each row specifies the charge on each electrode of the electrode array 18 (FIGS. 1 and 2) that the stimulation system determines should be applied to the patient for a particular purpose. The electrode array 18 preferably comprises eight or sixteen electrodes, but the measurement table may only utilize a subset of the electrode array 18, for example four electrodes. Those skilled in the art will recognize that a measurement table may include stimulation parameter sets with various variations, such as pulse duration or pulse frequency, and a measurement table with such other variations is intended to come within the scope of the present invention. An exemplary simplified measurement table that may be used with the invention is found in Appendix A.

The steering table, or equivalent, typically includes a larger number of rows than does the measurement table. An exemplary steering table, containing 541 rows, that may be used with the invention is found in Appendix B. The rows in the steering table typically reflect the same variation as the rows in the measurement table, however, those skilled in the art will recognize that the steering table may also include other degrees of variation not included in the measurement table, and these variations are also intended to come within the scope of the invention. At least one row in the steering table will however correspond to one of the rows in the measurement table, as will be made apparent by the following description.

The rows in the steering table are arranged in order based on the physical characteristics of the stimulation provided by each stimulation parameter set, so that moving from one row to the next in the steering table represents a gradual, and somewhat uniform, change in stimulation. In other words, stepping from one row to an adjacent row in the steering table causes the stimulation applied to the tissue through the individual electrodes of the electrode array 18 to gradually move in a desired direction. This type of current steering is described more fully in U.S. Pat. No. 6,393,325, incorporated herein by reference.

Once the desired measurement table and steering table have been provided, the first step in the method is selection of a trial stimulation parameter set (block 24). Generally, the first row of the measurement table will be tested first, followed in order by the remaining rows. However, the order of row selection is not essential, and the rows may be selected in any order. Next, the selected stimulation parameter set is used to provide stimulation to the patient (block 26). The patient provides feedback as to the effectiveness of the stimulation that has been applied using the trial stimulation parameter set. Alternative means (e.g., objective measurements of various physiological parameters of the patient, such as perspiration, muscle tension, respiration rate, heart rate, and the like) may also be used to judge the effectiveness of the applied stimulation. A determination is then made if all of the trial sets have been tested (block 28). The steps of selecting a trial set of stimulation parameters (block 24) and providing stimulation in accordance with the selected trial set of stimulation parameters (block 26) are repeated until all of the trial stimulation parameter sets have been tested.

After all of the trial stimulation parameter sets have been tested, the trial stimulation parameter sets are ranked (block 30) based upon the patient's evaluation (and/or based upon alternative evaluation of selected physiological parameters of the patient) of the effectiveness of each trial stimulation parameter set.

The testing and ranking of the trial stimulation parameter sets provides a coarse approximation of the stimulation which may be most effective. Because the trial stimulation parameter set is only a coarse approximation, the implication is that fine adjustments of such parameter sets may also be effective, and perhaps even more effective. Hence, once the trial stimulation parameter sets have been ranked, the highest ranked trial stimulation parameter set becomes a first specified ranked set that functions as a first "benchmark", or starting point, for a much finer search for the most effective stimulation parameter set. The finer search for a stimulation parameter set begins by selecting a row in the steering table that corresponds to the highest ranked set in the measurement table (block 32a). This selected highest ranked trial stimulation parameter set is then used to provide stimulation (block 34a) to the patient. Again, the patient evaluates the effectiveness of the stimulation, and/or alternative means (e.g., measuring physiological parameters of the patient) are used to evaluate the effectiveness of the stimulation. Then, a row next to the row just tested, e.g., moving in a first direction in the steering table, such as down, is selected as a possible new stimulation parameter set (block 36), and this new row is then used to provide stimulation (block 34b). The results of the new stimulation are then compared to the results of the previous stimulation (block 38a). If the results improve (YES branch of block 38a) the steps set forth in blocks 36 and 34b are repeated, i.e., the row in the steering table adjacent to the most recently used row, moving in the same direction in the table as before, is used to define a new stimulation parameter set (block 36) and that stimulation parameter set is used to provide stimulation (block 34b). As long as the stimulation results continue to improve, this process of stepping to the next row in the steering table and retesting is continued, thereby fine tuning the stimulation parameter set until no further improvements are detected.

As soon as the results fail to improve (NO branch of block 38), the method goes back to the "benchmark" parameter set, i.e., that row in the steering table corresponding to the highest ranked set (block 32b) and stimulation is again provided (block 34c). This is actually a repeat of the stimulation performed at blocks 32a and 34a, but inasmuch as one or more stimulation parameter sets have been provided since the benchmark stimulation was provided, at steps 32a and 34a, this repeat stimulation provides the patient with a reminder or refresher of what the benchmark stimulation was like. (Alternatively, of course, this repeat of the benchmark stimulation could be skipped.) Then, a process almost identical to that described above is performed to again fine tune the benchmark stimulation parameter set, only in the other direction. That is, the row adjacent to the row that defines the benchmark stimulation parameter set is selected as the row that defines the stimulation parameter set (block 40), moving in the opposite direction, e.g., up, from the direction used in the step performed at block 36. Once a row is selected, stimulation is provided using the parameters of the selected row (block 34d). Thus, the fine tuning that occurs at steps 40 and 34d in FIG. 3 occurs while moving in the opposite direction in the steering table than was used previously.

The results of the new stimulation applied at step 34d are compared to the results of the previous stimulation (block 38b). If the results improve (YES branch of block 38b), the steps set forth in blocks 40 and 34d are repeated, i.e., the row in the steering table adjacent to the most recently used row, moving in the same direction in the table as before, are used to define a new stimulation parameter set (block 40), and that stimulation parameter set is used to provide stimulation (block 34d). As long as the stimulation results continue to improve, this process of stepping to the next row in the steering table, and retesting is continued, thereby fine tuning the stimulation parameter set until no further improvements are detected.

Hence, it is seen that thus far in the method, two sets of effective stimulation parameters have been identified: one by moving in a first direction from the benchmark row (of the specified ranked set) in the steering table (determined using the steps at blocks 36, 34b and 38a), and another by moving from the benchmark row in a second direction in the steering table (determined using the steps at blocks 40, 34d and 38b). These two possible stimulation sets are then evaluated to see if one comprises the most effective stimulation set (block 42). If so (YES branch of block 42), then that set is selected as the best parameter stimulation set for the stimulation that is to be provided (block 46) whenever the operating program of the SCS system (or other neural system) determines stimulation is needed. If not (NO branch of block 42), then the search continues for the most effective stimulation set by selecting the row in the steering table corresponding to the next highest ranked set (block 44), e.g., the second ranked stimulation set. This next highest ranked set thus defines a new specified "benchmark" stimulation set from which additional fine tuning is performed as described above (blocks 32a through 38b).

It is thus seen that unless an effective stimulation parameter set is found at block 42, the process described in FIG. 3 is repeated for the next highest ranked trial stimulation parameter set, until the most effective stimulation parameter set is identified.

By way of a simple example, consider the Simplified Measurement Table found in Appendix A and the Simplified Steering Table found in Appendix B. After testing each of the stimulation parameter sets defined by the rows in the Simplified Measurement Table in Appendix A, the following "coarse" ranking in effectiveness of the stimulation sets is found:

| Stimulation Set | Rank |
|---|---|
| 3 | 1 |
| 1 | 2 |
| 2 | 3 |
| 4 | 4 |

Starting with the highest ranked Stimulation Set (from the Simplified Measurement Table in Appendix A), which uses Electrode Number 3 as an anode (+) and Electrode Number 5 as a cathode (−) to provide a stimulus to the patient, a corresponding row in the Simplified Steering Table (in Appendix B) is found to be Stimulation Set No. 301, which shows that the current flow from Electrode 3 is "1" and the current flow from Electrode 5 is "−1". This means that all of the current applied by the stimulator is applied from Electrode 3 as an anode to Electrode 5 as a cathode. (The amplitude of the current applied may, of course, be adjusted as required.) Thus, the coarse adjustment provided by the measurement table leads one to Stimulation Set No. 301 in the Simplified Steering Table. Stimulation Set No. 301 thus serves as the first "benchmark" stimulation set.

Once the first benchmark stimulation set is identified, the method then fine tunes this selection by applying the stimulation set(s) adjacent the benchmark set. For example, going "down" in the Simplified Steering Table, Stimulation Set No. 302 is applied, then No. 303, and then No. 304, and so on, until the patient (or other means) determines that no further improvement results. In this example, Stimulation Set No. 302 is found to be the most effective set.

In a similar manner, going "up" in the Simplified Steering Table from the benchmark set (No. 301), Stimulation Set No. 300 is applied, then No. 299, then No. 298, and so on, until the patient (or other means) determines that no further improvement results. In this example, Stimulation Set 298 is found to be the most effective set to use.

Once, the two Stimulation Sets No. 298 and 302 have been identified, then a determination is made as to which one is the most effective to use for stimulation. If one of these two is the most effective, e.g., Stimulation Set No. 298, then that Stimulation Set is selected as the best one to use for stimulation in this instance, and the search ends. If, however, neither is found to be the most effective, then the process continues by locating the second-highest ranked benchmark stimulation set (corresponding to Stimulation Set No. 1 in the Simplified Measurement Table) in the Simplified Steering Table. As seen from the Simplified Measurement Table, Stimulation Set No. 1 defines Electrode No. 1 as a cathode and Electrode No. 3 as an anode. This corresponds to Stimulation Set No. 21 in the Simplified Steering Table. Hence, fine tuning of this benchmark stimulation set is conducted by first going "down", and then "up" from Stimulation Set No. 21 until the stimulation set is found that does not result in any further improvement.

The two stimulation sets identified from fine tuning the second benchmark stimulation set (one by moving "down" from the benchmark row and the other by moving "up" from the benchmark row) are then evaluated to determine if one is the most effective to use for stimulation. If one of these two is the most effective, then that stimulation set is selected as the best one to use for stimulation in this instance, and the search ends. If, however, neither is found to be the most effective, then the process continues by locating the third-highest ranked benchmark stimulation set (corresponding to Stimulation Set No. 2 in the Simplified Measurement Table) in the Simplified Steering Table, and the process continues as described.

Those skilled in the art will recognize that various variations exist to the method described herein. For example. A gradient method may be utilized to evaluate the slope of stimulation parameter set effectiveness around each trial stimulation parameter set. A combination of the relative effectiveness of each trial stimulation parameter set, and the slope of the effectiveness in the neighborhood of the trial stimulation parameter set may be used to select which trial stimulation parameter set to test around. The basic core of the present invention is to use a table, or equivalent, of a small number of trial stimulation parameter sets (a coarse table) to determine a starting point, and a larger table (a fine table), or equivalent, of predetermined stimulation parameter sets to guide the search for a local optimum. Any method for finding an effective stimulation parameter set that uses a combination of a small course table, and a large fine table, is intended to come within the scope of the invention.

While the invention herein disclosed has been described by means of specific embodiments and applications thereof, numerous modifications and variations could be made thereto by those skilled in the art without departing from the scope of the invention set forth in the claims.

What is claimed is:

1. A method for selecting a stimulation parameter set for use in an implantable neural stimulator, comprising:
   providing a set of stimulation parameter sets;
   providing a set of trial stimulation parameter sets within the set of stimulation parameter sets;
   wherein at least one of the set of stimulation parameter sets and the set of trial stimulation parameter sets are organized in a table, wherein each row of the table defines a charge on each electrode of an electrode array;
   testing each of the trial stimulation parameter sets;
   testing members of the set of stimulation parameter sets based on the results of testing the trial stimulation parameter sets; and
   selecting a stimulation parameter set based on the results of testing members of the stimulation parameter sets.

2. The method of claim 1 wherein providing a set of stimulation parameter sets and providing a set of trial stimulation parameter sets comprises:
   providing a measurement table wherein each row of the measurement table defines a charge on each electrode of an electrode array.

3. The method of claim 2 wherein providing a measurement table for the set of trial stimulation parameter sets comprises:
   providing a measurement table comprising at least four rows and not more than sixteen rows.

4. The method of claim 1 wherein testing each of the trial stimulation parameter sets comprises:
   selecting a selected trial stimulation parameter set from the trial stimulation parameter sets;
   applying stimulation using the selected trial stimulation parameter set; and
   repeating the selecting and stimulating until all of the trial stimulation parameter sets have been tested.

5. The method of claim 4 further including ranking the trial stimulation parameter sets following testing each of the trial stimulation parameter sets.

6. The method of claim 5 wherein ranking the trial stimulation parameter sets comprises:
   ordering the trial stimulation parameter sets from the best to the worst based on the effectiveness of each of the trial stimulation parameter sets.

7. The method of claim 6 wherein ordering the trial stimulation parameter sets from the best to the worst based one the effectiveness of each of the trial stimulation parameter sets comprises:
   ordering the trial stimulation parameter sets from the best to the worst based on the effectiveness of each of the trial stimulation parameter sets as described by a patient who receives the applied stimulation.

8. The method of claim 5 wherein testing members of a set of stimulation parameter sets based on the results of testing the trial stimulation parameter sets comprises:
   obtaining an ordered set of stimulation parameter sets, wherein the stimulation parameter sets are ordered based on the physical characteristics of the stimulation provided by each stimulation parameter set;
   selecting a selected stimulation parameter set with physical characteristics closest to the highest ranked trial stimulation parameter set;
   stimulating the patient with the selected stimulation parameter set;
   selecting a new selected stimulation parameter set adjacent to the previous selected stimulation parameter set;
   comparing the results of stimulation using the new selected stimulation parameter set to the results of stimulation using the previous selected stimulation parameter set;
   repeating selecting a new selected stimulation parameter set and comparing the results of stimulation until the result of stimulation with the new selected stimulation parameter set is not as good as the results of stimulation with the previous selected parameter set; and
   selecting the stimulation parameter set that provides the best results.

9. The method of claim 8 wherein providing a set of stimulation parameter sets comprises:
   providing a steering table wherein each row of the steering table defines a charge on each electrode of an electrode array, wherein the rows in the steering table are ordered based on the physical characteristics of the stimulation provided by each row.

10. The method of claim 9 wherein selecting a new selected stimulation parameter set adjacent to the previous selected stimulation parameter set comprises:
   selecting a row in the steering table next to the previous row.

11. The method of claim 10 further including, before selecting the stimulation parameter set that provided the best results:
   repeating the process of finding the best stimulation parameter set, moving in the opposite direction in the steering table.

12. The method of claim 11 further including:
   if an effective stimulation parameter set is not found, repeating the search for the best stimulation parameter set based on the next highest ranked trial stimulation parameter set.

13. A method for selecting a stimulation parameter set for use within an implantable neural stimulator, comprising:
   providing a measurement table comprising rows containing trial stimulation parameter sets defining a charge on each electrode of an electrode array;
   providing a steering table comprising rows containing stimulation parameter sets defining a charge on each electrode of the electrode array, wherein the rows further comprise an ordered set of stimulation parameter sets, wherein the stimulation parameter sets are ordered based on the physical characteristics of the stimulation provided by each stimulation parameter set;
   testing each of the trial stimulation parameter sets;
   ranking each of the trial stimulation parameter sets;
   selecting the best trial stimulation parameter set;
   testing members of the set of stimulation parameter sets based on the results of testing the trial stimulation parameter sets; and
   selecting a row in the steering table comprising the stimulation parameter set with physical characteristics closest to the highest ranked trial stimulation parameter set;
   applying stimulation using the selected stimulation parameter set;
   selecting a new row in the steering table next to the previously selected row;
   comparing the results of stimulation using the new selected row of the simplified steering table to the results of stimulation using the previous selected row of the simplified steering table;
   repeating selecting a new row and comparing the results of stimulation until the result of stimulation with the row is not as good as the results of stimulation with the previous row;
   repeating the selecting and comparing, moving in the opposite direction in the steering table; and
   selecting a suitable stimulation parameter set that provides the most effective results.

14. The method of claim 13 wherein, if a suitable stimulation parameter set is not found, repeating the search for a suitable stimulation parameter set based on the next highest ranked trial stimulation parameter set.

15. In an implantable neural stimulator having means for storing a stimulation parameter set that controls the stimulation provided by the stimulator, a method for selecting one stimulation parameter set from a large number of possible stimulation sets for use by the neural stimulator comprising the steps of:
   testing a small number of stimulation parameter sets within the large number of possible stimulation sets to determine a starting point for making a final selection of a stimulation set, wherein the stimulation parameter sets are organized in a table, wherein each row of the table defines a charge on each electrode of an electrode array;
   ranking the tested stimulation parameter sets; and
   searching for a local optimum stimulation parameter set in the vicinity of highest-ranked tested stimulation parameter sets.

16. A method for selecting a stimulation parameter set for use in an implantable neural stimulator, comprising:
   providing a set of stimulation parameter sets;
   providing a set of trial stimulation parameter sets within the set of stimulation parameter sets;
   testing each of the trial stimulation parameter sets;
   testing members of the set of stimulation parameter sets based on the results of testing the trial stimulation parameter sets, wherein the stimulation parameter sets are ordered based on the physical characteristics of the stimulation provided by each stimulation parameter set; and
   selecting a stimulation parameter set based on the results of testing members of the stimulation parameter sets.

17. The method of claim 16 wherein providing a set of trial stimulation parameter sets comprises:
   providing a measurement table wherein each row of the measurement table defines a charge on each electrode of an electrode array.

18. The method of claim 17 wherein providing a measurement table comprises:
   providing a measurement table comprising at least four rows and not more than sixteen rows.

19. The method of claim 16 wherein testing each of the trial stimulation parameter sets comprises:
selecting a selected trial stimulation parameter set from the trial stimulation parameter sets;
applying stimulation using the selected trial stimulation parameter set; and
repeating the selecting and stimulating until all of the trial stimulation parameter sets have been tested.

20. The method of claim 19 further including ranking the trial stimulation parameter sets following testing each of the trial stimulation parameter sets.

21. The method of claim 20 wherein ranking the trial stimulation parameter sets comprises:
ordering the trial stimulation parameter sets from the best to the worst based on the effectiveness of each of the trial stimulation parameter sets.

22. The method of claim 21 wherein ordering the trial stimulation parameter sets from the best to the worst based one the effectiveness of each of the trial stimulation parameter sets comprises:
ordering the trial stimulation parameter sets from the best to the worst based on the effectiveness of each of the trial stimulation parameter sets as described by a patient who receives the applied stimulation.

23. The method of claim 22 wherein testing members of a set of stimulation parameter sets based on the results of testing the trial stimulation parameter sets comprises:
obtaining a ordered set of stimulation parameter sets, wherein the stimulation parameter sets are ordered based on the physical characteristics of the stimulation provided by each stimulation parameter set;
selecting a selected stimulation parameter set with physical characteristics closest to the highest ranked trial stimulation parameter set;
stimulating the patient with the selected stimulation parameter set;
selecting a new selected stimulation parameter set adjacent to the previous selected stimulation parameter set;
comparing the results of stimulation using the new selected stimulation parameter set to the results of stimulation using the previous selected stimulation parameter set;
repeating selecting a new selected stimulation parameter set and comparing the results of stimulation until the result of stimulation with the new selected stimulation parameter set is not as good as the results of stimulation with the previous selected parameter set; and
selecting the stimulation parameter set that provides the best results.

24. The method of claim 23 wherein providing a set of stimulation parameter sets comprises:
providing a steering table wherein each row of the steering table defines a charge on each electrode of an electrode array, wherein the rows in the steering table are ordered based on the physical characteristics of the stimulation provided by each row.

25. The method of claim 24 wherein selecting a new selected stimulation parameter set adjacent to the previous selected stimulation parameter set comprises:
selecting a row in the steering table next to the previous row.

26. The method of claim 25 further including, before selecting the stimulation parameter set that provided the best results:
repeating the process of finding the best stimulation parameter set, moving in the opposite direction in the steering table.

27. The method of claim 26 further including:
if an effective stimulation parameter set is not found, repeating the search for the best stimulation parameter set based on the next highest ranked trial stimulation parameter set.

28. A method for selecting a stimulation parameter set for use within an implantable neural stimulator, comprising:
providing a measurement table comprising rows containing trial stimulation parameter sets defining a charge on each electrode of an electrode array;
providing a steering table comprising rows containing stimulation parameter sets defining a charge on each electrode of the electrode array, wherein the rows further comprise an ordered set of stimulation parameter sets, wherein the stimulation parameter sets are ordered based on the physical characteristics of the stimulation provided by each stimulation parameter set;
testing each of the trial stimulation parameter sets;
ranking each of the trial stimulation parameter sets;
selecting the best trial stimulation parameter set;
testing members of the set of stimulation parameter sets based on the results of testing the trial stimulation parameter sets; and
selecting a row in the steering table comprising the stimulation parameter set with physical characteristics closest to the highest ranked trial stimulation parameter-set;
applying stimulation using the selected stimulation parameter set;
selecting a new row in the steering table next to the previously selected row;
comparing the results of stimulation using the new selected row of the simplified steering table to the results of stimulation using the previous selected row of the simplified steering table;
repeating selecting a new row and comparing the results of stimulation until the result of stimulation with the row is not as good as the results of stimulation with the previous row;
repeating the selecting and comparing, moving in the opposite direction in the steering table; and
selecting a suitable stimulation parameter set that provides the most effective results.

29. The method of claim 28 wherein, if a suitable stimulation parameter set is not found, repeating the search for a suitable stimulation parameter set based on the next highest ranked trial stimulation parameter set.

30. In an implantable neural stimulator having means for storing a stimulation parameter set that controls the stimulation provided by the stimulator, a method for selecting one stimulation parameter set from a large number of possible stimulation sets for use by the neural stimulator comprising the steps of:
testing a small number of stimulation parameter sets within the large number of possible stimulation sets to determine a starting point for making a final selection of a stimulation set, wherein the tested stimulation parameter sets are ordered based on the physical characteristics of the stimulation provided by each stimulation parameter set;
ranking the tested stimulation parameter sets; and
searching for a local optimum stimulation parameter set in the vicinity of highest-ranked tested stimulation parameter sets.

* * * * *